United States Patent [19]
Kalidindi

[11] Patent Number: 5,823,592
[45] Date of Patent: Oct. 20, 1998

[54] FLEXIBLE SWABBING TOOL

[76] Inventor: Sanyasi Raju Kalidindi, P.O. Box 10837, New Brunswick, N.J. 08906-9998

[21] Appl. No.: 671,731

[22] Filed: Jun. 28, 1996

[51] Int. Cl.$^6$ ................................ B25J 1/02; B25J 15/04
[52] U.S. Cl. ...................... 294/24; 15/144.4; 15/210.1; 73/864.71; 294/19.1
[58] Field of Search ............................. 294/19.1, 22–24, 294/99.2, 104, 106; 15/104.94, 105, 118, 144.1, 144.4, 146, 150, 160, 210.1, 231, 145; 16/115; 81/53.1, 53.11, 53.12; 403/348, 349; 73/863, 864, 864.31, 864.71, 864.91

[56] References Cited

U.S. PATENT DOCUMENTS

| | | | |
|---|---|---|---|
| 721,480 | 2/1903 | Van Schott | 294/99.2 X |
| 977,158 | 11/1910 | Berkstresser | 81/53.11 |
| 2,716,043 | 8/1955 | Baril | 294/19.1 X |
| 3,215,006 | 11/1965 | Urani | 294/99.2 X |
| 3,276,087 | 10/1966 | Hanson | 294/19.1 X |
| 3,423,781 | 1/1969 | Henson | 403/349 X |
| 3,430,496 | 3/1969 | Swanberg et al. . | |
| 3,841,973 | 10/1974 | Wilkins et al. . | |
| 4,033,618 | 7/1977 | Lamb | 294/19.1 |
| 4,202,067 | 5/1980 | Stamatovic . | |
| 4,986,207 | 1/1991 | Reed | 294/19.1 X |
| 5,188,332 | 2/1993 | Callas | 294/19.1 X |
| 5,251,496 | 10/1993 | Platek . | |
| 5,312,536 | 5/1994 | Pai et al. . | |
| 5,373,748 | 12/1994 | Lioy et al. . | |
| 5,395,188 | 3/1995 | Bailey et al. . | |
| 5,396,178 | 3/1995 | Rybarski . | |

FOREIGN PATENT DOCUMENTS 2280133  1/1995  United Kingdom .

*Primary Examiner*—Johnny D. Cherry
*Attorney, Agent, or Firm*—Richard C. Litman

[57] ABSTRACT

A swabbing tool with a telescoping handle and a flexible tubular extension ending in a socket within which a variety of attachments can be inserted, to take swab samples of remote and distant surfaces, without someone having to actually climb up or go down to the surfaces, to determine whether a surface has been adequately cleaned. The clamp attachment has pivotally connected upper and lower members, which each have a jaw extending beyond a recess. There is a notch in the center of the jaws for holding swabs with narrow cylindrical handles. There are also attachments having a template with a hole of a known area. A swab on another handle must be used to take a sample within the hole of a surface which the template is held against. Extending from the rear of either kind of attachment is a cylindrical member, which fits inside the socket. Extending from the cylindrical member is a fixed peg, and a depressible peg which is biased outward by a spring in the cylindrical member, but which is pushed inward when the cylindrical member is inserted into the socket. The socket has a curved notch, within which the fixed peg of a cylindrical member fits. The outward bias of the depressible peg helps retain the fixed peg in the curved notch, and thereby helps keep the cylindrical member in the socket.

5 Claims, 9 Drawing Sheets

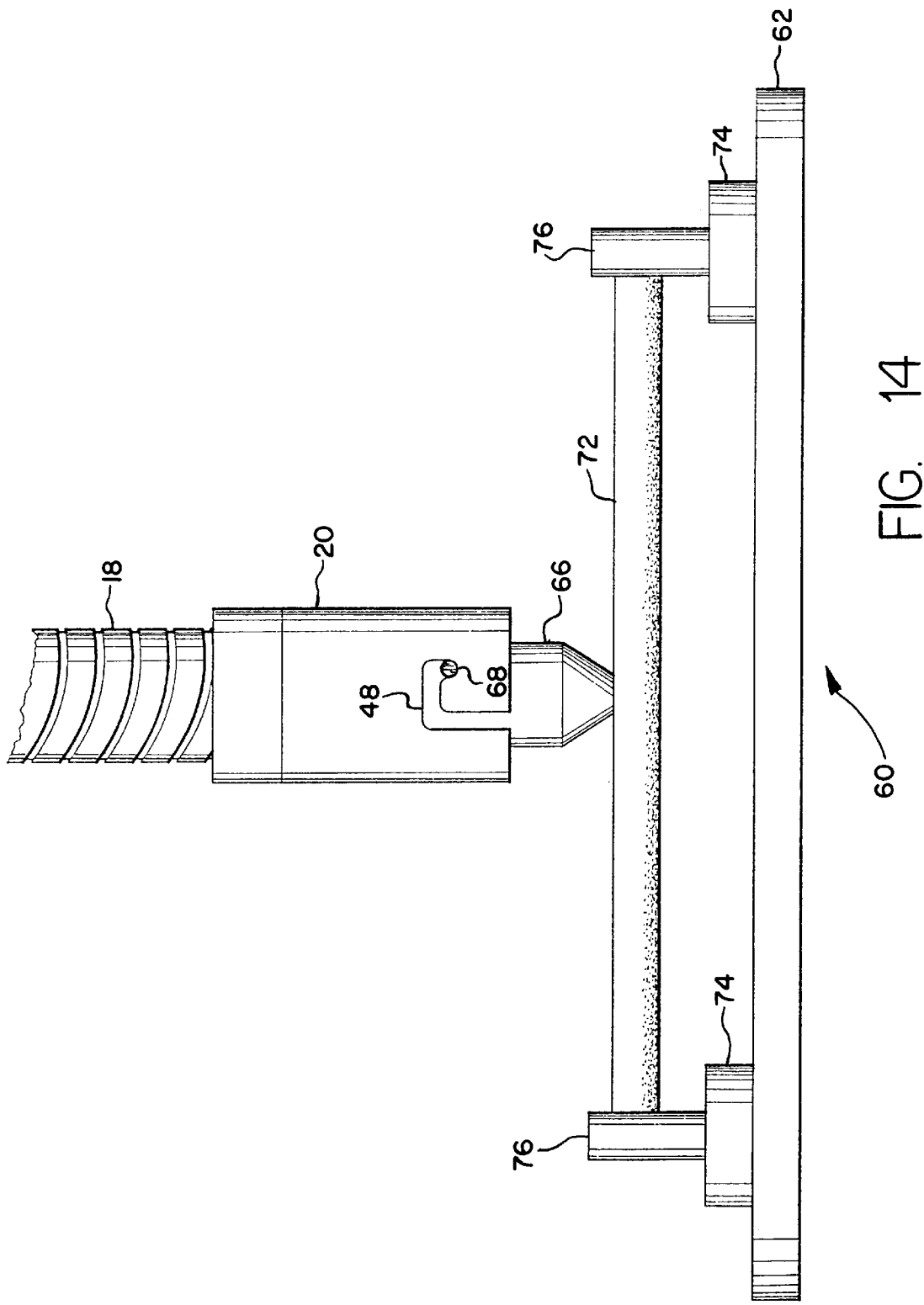

FLEXIBLE SWABBING TOOL

BACKGROUND OF THE INVENTION

1. Field of the Invention

The present invention relates to a tool for taking swab samples from surfaces to validate cleaning.

2. Description of the Prior Art

When doing cleaning validation in a pharmaceutical, food, cosmetic, medical, electronic or chemical industry, there are often remote and distant surfaces from which samples should be taken. It is also desirable to be able to take surface samples of these remote and distant locations without someone having to actually climb up or go down to them. It is also desirable to be able to take samples of a known surface area so that the contamination on the entire surface in question may be accurately quantified. It is furthermore desirable that any tool to meet these needs be light weight, easy to use, and versatile. The present invention meets these criteria, with a telescoping handle having a flexible extension ending in a socket to which a variety of tools can be attached. A clamp attachment can hold a variety of sampling materials and devices, and is configured to reduce contact with absorbent material used for swab samples, and thereby contamination with previous material sampled. Template attachments may also be used to swab within an area of known size.

U.S. Pat. No. 3,430,496, issued on Mar. 4, 1969, to Stacy C. Swanberg and Donald C. Bohlsen, discloses a contamination sampler, with an elongated handle and a foot across which an absorbent tape passes between two reels. The foot with the tape is pressed against a surface to be sampled for radioactive contamination. The instant invention is distinguishable, in that absorbent material is held between jaws rather than between reels, there is a socket into which various sampling devices can be removably inserted, and its handle can be folded up like a telescope.

U.S. Pat. No. 3,841,973, issued on Oct. 15, 1974, to Judd R. Wilkins and Stacey M. Mills, discloses an apparatus for microbiological sampling, with a motor driven cart, on which a second motor is carried for moving a swabbing device across a surface. The instant invention is distinguishable, in that it is hand held, and has a socket with several attachments for swabbing.

U.S. Pat. No. 4,202,067, issued on May 13, 1980, to Bosko Stamatovic, discloses a motorized work device with a flexible shaft, for providing an angularly displaceable work tool at a point remote from a power source. The instant invention is readily distinguishable, as it is not motorized.

U.S. Pat. No. 5,251,496, issued on Oct. 12, 1993, to Gary F. Platek, discloses a surface sampling tester, which exposes a surface to a rinsing agent, and then collects the rinsing agent. The instant invention is distinguishable, in that it does not require the use of a rinsing agent to sample material on a surface.

U.S. Pat. No. 5,312,536, issued on May 17, 1994, to Deepak K. Pai and Gene A. Maday, discloses a method and apparatus to evaluate the effectiveness of cleaning systems for high density electronics, in which a contaminant is placed between two glass plates, which are then subjected to a cleaning process. While the instant invention might also be used to evaluate the effectiveness of a cleaning process, by swabbing a surface after it has been cleaned, it does not require that contaminants be placed between two surfaces before cleaning.

U.S. Pat. No. 5,373,748, issued on Dec. 20, 1994, to Paul J. Lioy and Clifford P. Weisel, discloses a wipe template sampler, with a template having an aperture which exposes a testing surface of a predetermined area, and a dust pick-up element to be used within that area. The instant invention is distinguishable, in that it has a socket at the end of a flexible arm extending from a telescoping handle, into which various attachments can be inserted, including a clamp with jaws for holding absorbent material to collect samples.

U.S. Pat. No. 5,395,188, issued on Mar. 7, 1995, to Charles E. Bailey and Roy E. Bowling, discloses a guide for angled and curved drilling, including a curved guide tube, and a flexible shaft extending through the guide tool having a drill bit. While the instant invention has a flexible tubular portion, it is not designed for drilling.

U.S. Pat. No. 5,396,178, issued on Mar. 7, 1995, to Robert J. Rybarski, discloses an apparatus and method for determining that equipment is clean, by comparing the electrical conductivity of liquid used to rinse equipment, before and after the rinse. The instant invention does not require rinsing or measurements of electrical conductivity.

United Kingdom Patent Application No. 2,280,133, published Jan. 25, 1995, discloses an abrasive instrument for sample collection, in which a sample to be analyzed is removed by abrasion. The instant invention is distinguishable, in that it does not require abrasion to take a sample, and it has a telescoping handle, joined to a flexible extension ending in a socket, into which a variety of attachments for sample collection can be inserted, including a clamp with jaws for holding absorbent material.

None of the above inventions and patents, taken either singly or in combination, is seen to describe the instant invention as claimed.

SUMMARY OF THE INVENTION

The present invention is a swabbing tool with a telescoping handle and a flexible tubular extension ending in a socket within which a variety of attachments can be inserted, to take swab samples to determine whether a surface or an object has been adequately cleaned. The clamp attachment has pivotally connected upper and lower members, which each have a jaw extending beyond a recess. There is a notch in the center of the jaws for holding swabs with narrow cylindrical handles. There are also attachments having a template with a hole of a known area. Extending from the rear of either kind of attachment is a cylindrical member, which fits inside the socket. Extending from the cylindrical member is a fixed peg, and a depressible peg which is biased outward by a spring in the cylindrical member, but which is pushed inward when the cylindrical member is inserted into the socket. The socket has a curved notch, within which the fixed peg of a cylindrical member fits. The outward bias of the depressible peg helps retain the fixed peg in the curved notch, and thereby helps keep the cylindrical member in the socket.

Accordingly, it is a principal object of the invention to provide a new and improved means of cleaning validation of remote and distant surfaces, without someone having to actually climb up or go down to said surfaces.

It is another object of the invention to provide a socket and cylindrical insert which may be easily joined and separately, yet securely attached.

It is a further object of the invention to provide a means for holding absorbent material that reduces contamination from previous sampling.

Still another object of the invention is to provide a means for taking swab samples within a part of a surface of known area.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

FIG. 14 is a top view of the circular sample collection attachment attached to the flexible swabbing tool.

Similar reference characters denote corresponding features consistently throughout the attached drawings.

DETAILED DESCRIPTION OF THE PREFERRED EMBODIMENTS

The present invention is a swabbing tool with a telescoping handle and a flexible tubular extension ending in a socket within which a variety of attachments can be inserted. The purpose of the invention is cleaning validation; i.e., to determine whether remote and distant surfaces have been adequately cleaned, without someone having to actually climb up or go down to them.

Figure 1:
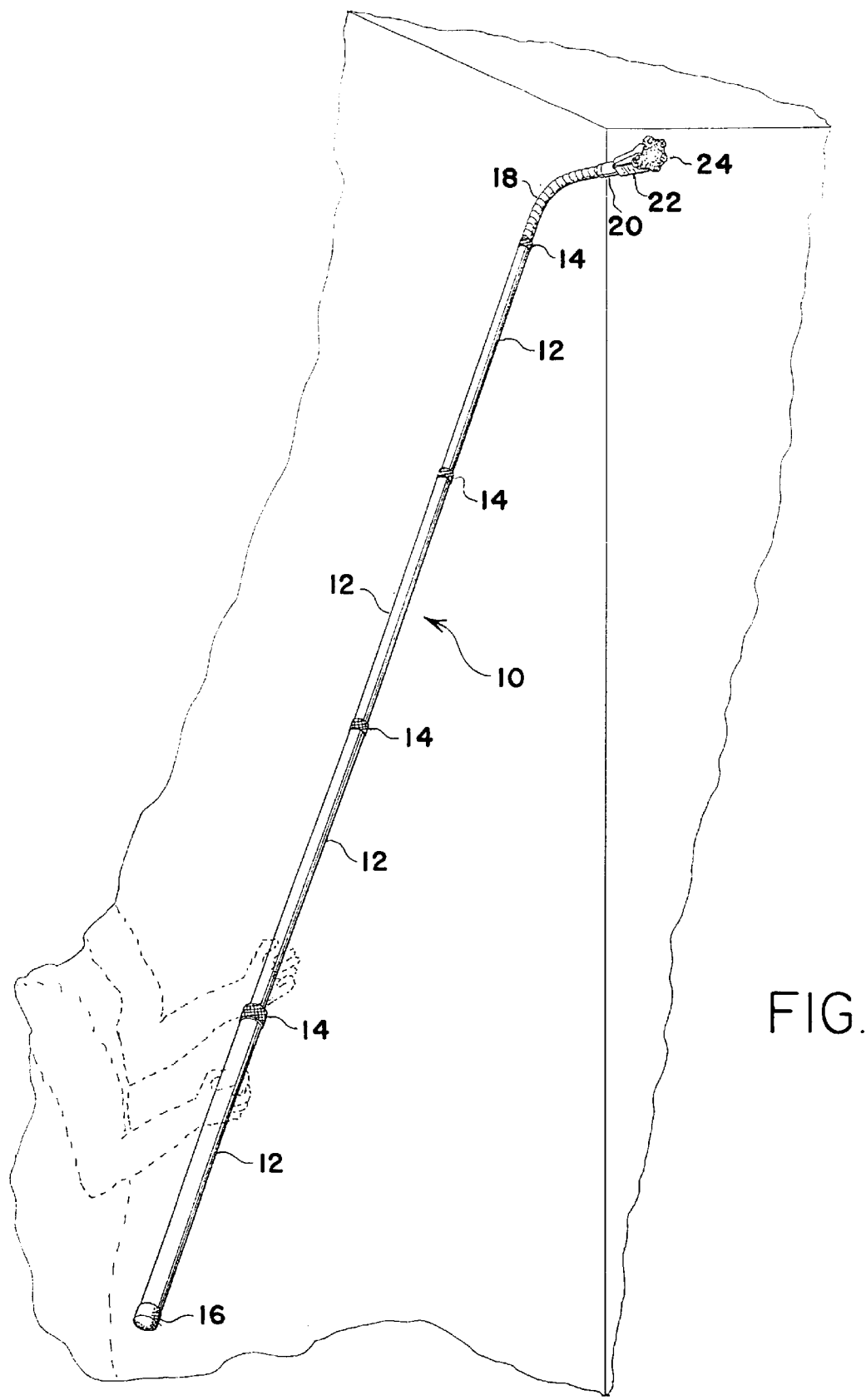
FIG. 1 is an environmental view of the invention.

FIG. 1 is an environmental view of the invention 10, showing it being used to take a swab from near the corner of a ceiling. The invention includes several telescoping handle members 12, each of which has a clamping ring 14 at its top end, which can be turned clockwise to fix the member above in a certain position, or turned counterclockwise to release it from a position. A bottom seal 16 keeps out dirt, moisture and other contaminants from the interior of the handle members. A flexible tubular portion 18 can be manually bent into a desired position, and will tend to retain that position until it is bent again. At the opposite end of the flexible tubular portion from where it is attached to the highest and smallest telescoping handle member is a socket 20, into which a variety of attachments can be inserted, including clamping attachment 22, which is holding a clump of absorbent material 24, such as cotton, to swab the surface of the ceiling.

Figure 2:
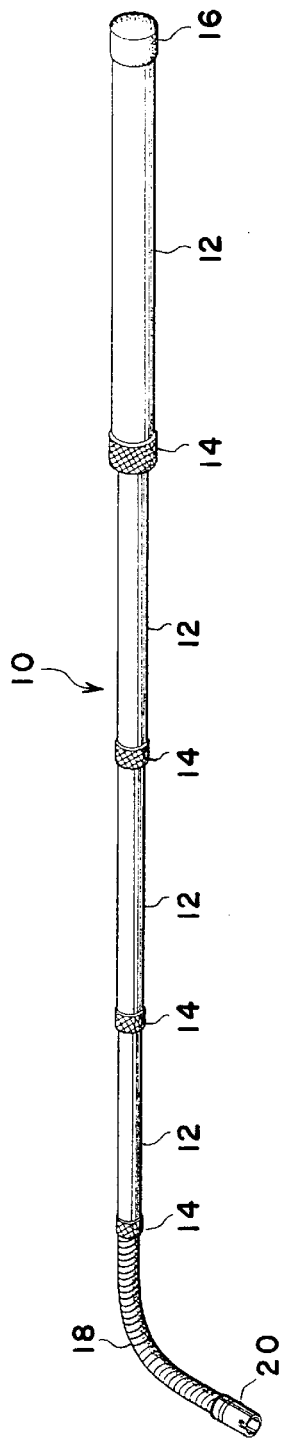
FIG. 2 is a perspective view of the invention, with its telescoping portion extended and its neck bent.
Figure 3:
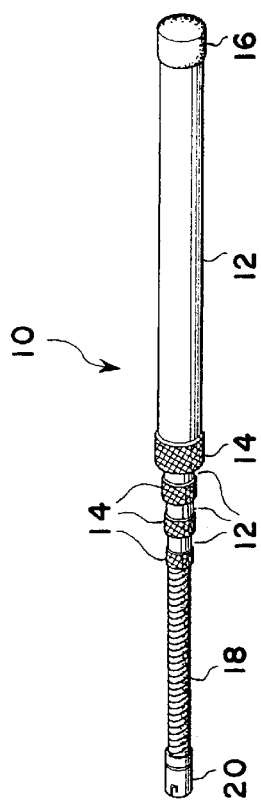
FIG. 3 is a perspective view of the invention, with its telescoping portion retracted and its neck straight.

FIG. 2 is a perspective view of the invention 10, with its telescoping handle members 12 fully extended, its neck 18 bent, and its socket 20 empty of any attachment. FIG. 3 is a perspective view of the invention, with its telescoping portion retracted, and its neck straight, showing how each handle member nests inside the adjacent handle member nearer the bottom.

Figure 4:
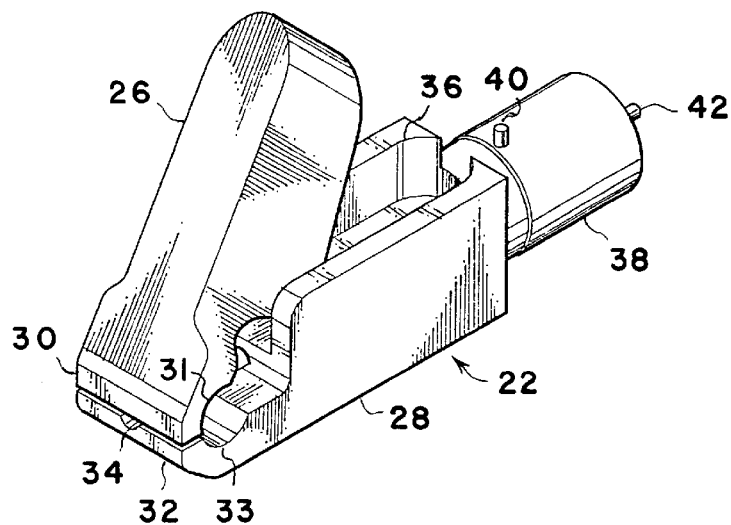
FIG. 4 is a perspective view of the clamp attachment in a closed position.
Figure 5:
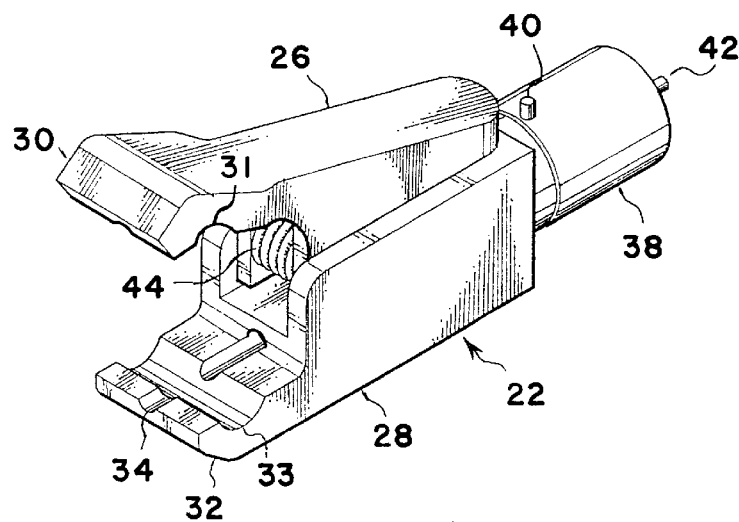
FIG. 5 is a perspective view of the clamp attachment in an open position.
Figure 6:
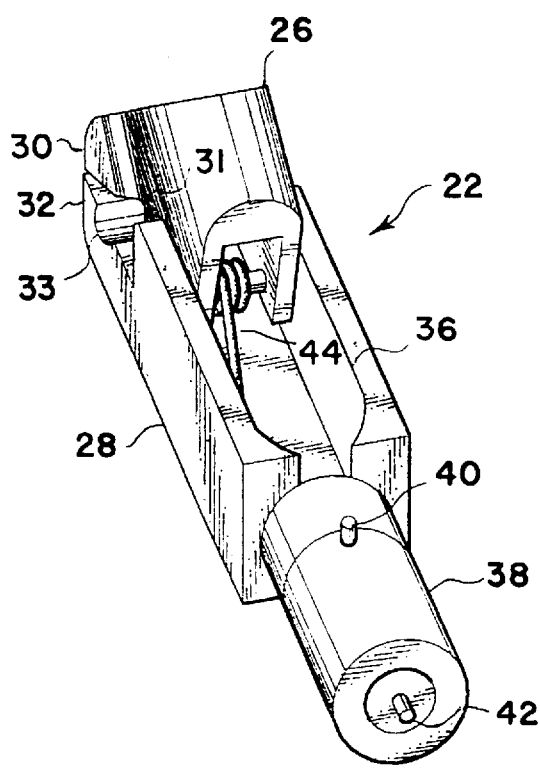
FIG. 6 is a perspective view of the clamp attachment in a closed position, seen from the rear.

FIG. 4 is a perspective view of the clamp attachment 22 in a closed position. The clamp attachment has an upper member 26 and a lower member 28. An upper jaw 30 extends beyond a recess 31 in the upper member. A lower jaw 32 extends beyond a recess 33 in the lower member. The narrow contact surfaces of the jaws and the recesses 31 and 33 extending parallel the length of the narrow contact surfaces of jaws 30 and 32 help minimize contact with the absorbent material being used to collect swab samples, and thus minimize contamination of the sample with material left on the clamp attachment from previous swabs. There is a notch 34 in the center of each jaw perpendicular to each recess for holding swabs with narrow cylindrical handles, such as Q-TIPS® cut in half. This notch extends into the lower member 28 of the clamp attachment 22, so that the distal end of the cylindrical handle of the swab fits into the notch, thus preventing lateral or vertical movement of the swab when using it to collect samples. There is a rear recess 36 within which the rear of the upper member can fit when it is depressed to open the jaws. Extending from the rear of the lower member is a cylindrical member 38, which fits inside the previously mentioned socket. Extending from the cylindrical member is a fixed peg 40, and a depressible peg 42, which is biased outward by a spring (not shown) in the cylindrical member, but which is pushed inward when the cylindrical member is inserted into the socket. FIG. 5 is a perspective view of the clamp attachment in an open position, showing the spring 44, which is attached around the pivotal connection between the upper and lower members. The spring gives the clamp attachment a bias towards the closed position. FIG. 6 is a perspective view of the clamp attachment in a closed position, seen from the rear.

Figure 7:
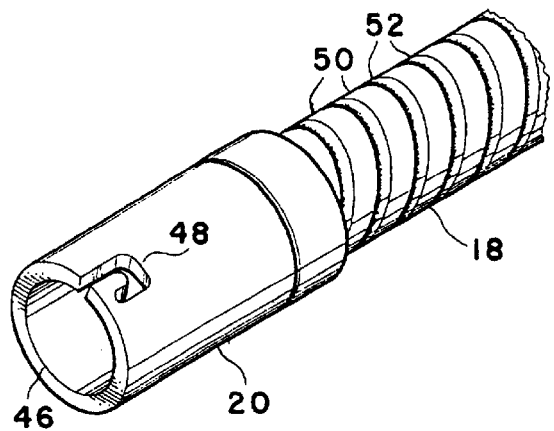
FIG. 7 is a detail view of the socket at the end of the neck that holds the attachments.

FIG. 7 is a detail view of the socket 20 at the end of the neck 18 that holds the attachments, showing the cavity 46 within which the aforementioned cylindrical members of the attachment fit. The socket has a curved or J-shaped notch 48, within which the fixed peg of a cylindrical member fits. The outward bias of the depressible peg helps retain the fixed peg in the curved notch, and thereby helps keep the cylindrical member in the socket. The neck has a spiral band 50, between the coils of which is a groove 52, so that the neck can be manually bent, but will tend to retain the position into which it has last been bent. The neck may be covered with a flexible plastic cover (not shown in the drawings) to keep dust, moisture and contamination out of its groove.

Figure 8:
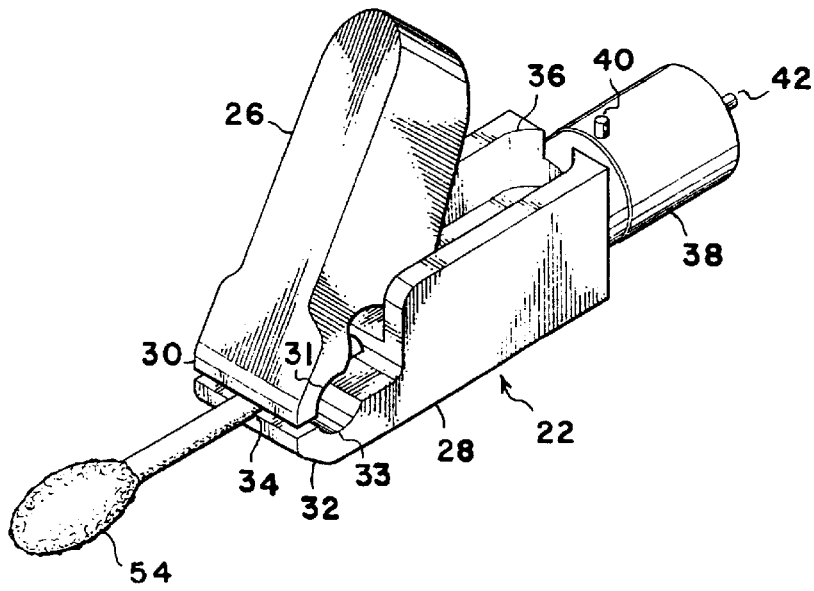
FIG. 8 is a perspective view of the clamp attachment in a closed position, holding a cotton swab.

FIG. 8 is a perspective view of the clamp attachment in a closed position, holding a polyester swab 54 in notch 34. It can be seen that the notch enables such a swab to be held firmly in the clamp attachment by its narrow cylindrical handle.

Figure 9:
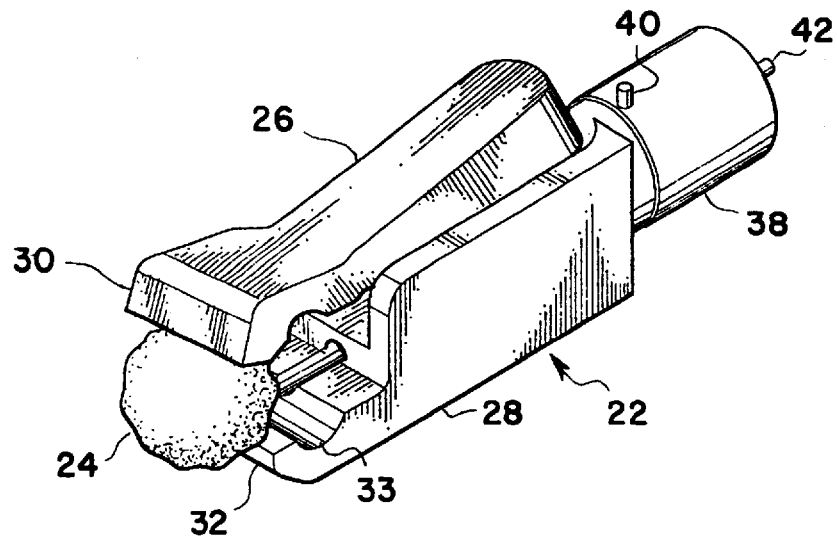
FIG. 9 is a perspective view of the clamp attachment in a semi-closed position, holding a clump of absorbent material.

FIG. 9 is a perspective view of the clamp attachment in a semi-closed position, holding a polyester swab 24. It can be seen how the narrow contact surfaces of the jaws 30 and 32 and the recesses 31 and 33 help minimize contact with the absorbent material being used to collect swab samples, and thus minimize contamination of the sample with material left on the clamp attachment from previous swabs.

Figure 10:
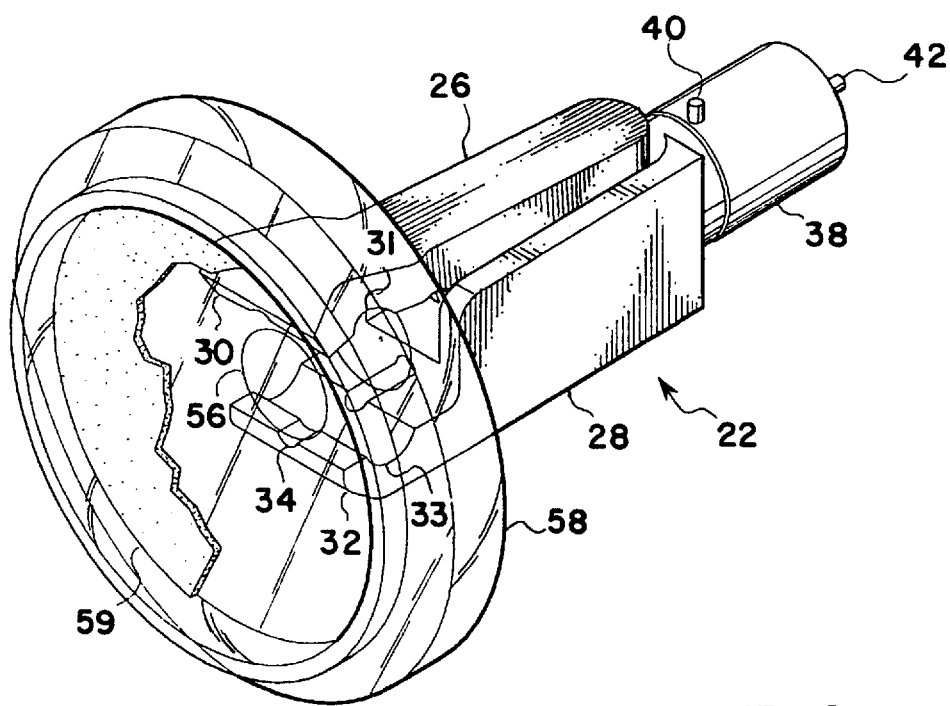
FIG. 10 is a perspective view of the clamp attachment in a semi-closed position, holding a suction cup that is holding a round sample collecting plate.

FIG. 10 is a perspective view of the clamp attachment in a semi-closed position, holding a suction cup 56 that is holding a round sample collecting plate 58. The sample collecting plate has a layer of a microbiological medium 59, shown partially cut away, on which microorganisms taken in the samples collected can be cultured. Both the notch 34 and the recesses 31 and 33 make it easier for the jaws 30 and 32 to hold the handle of the suction cup.

Figure 11:
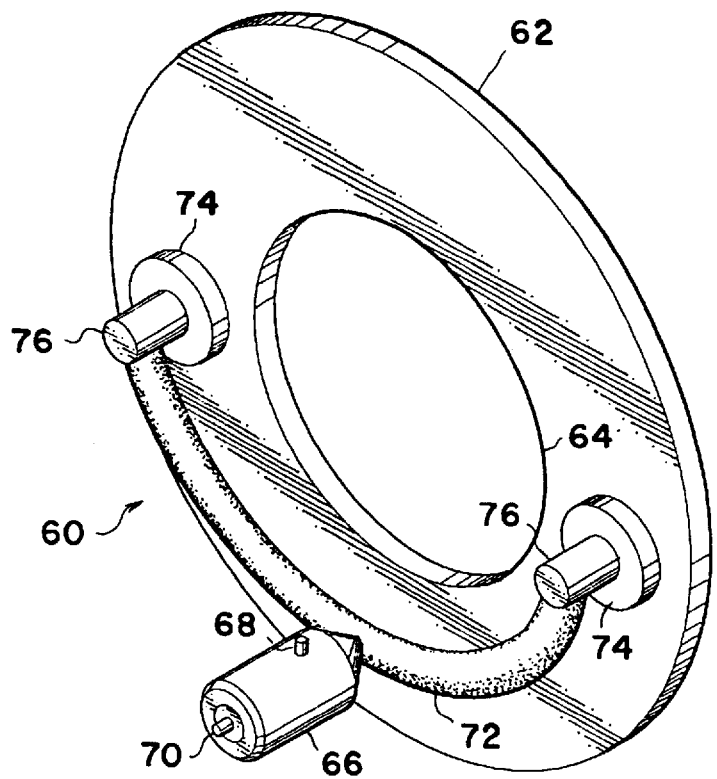
FIG. 11 is a perspective view of the circular sample collection attachment.
Figure 12:
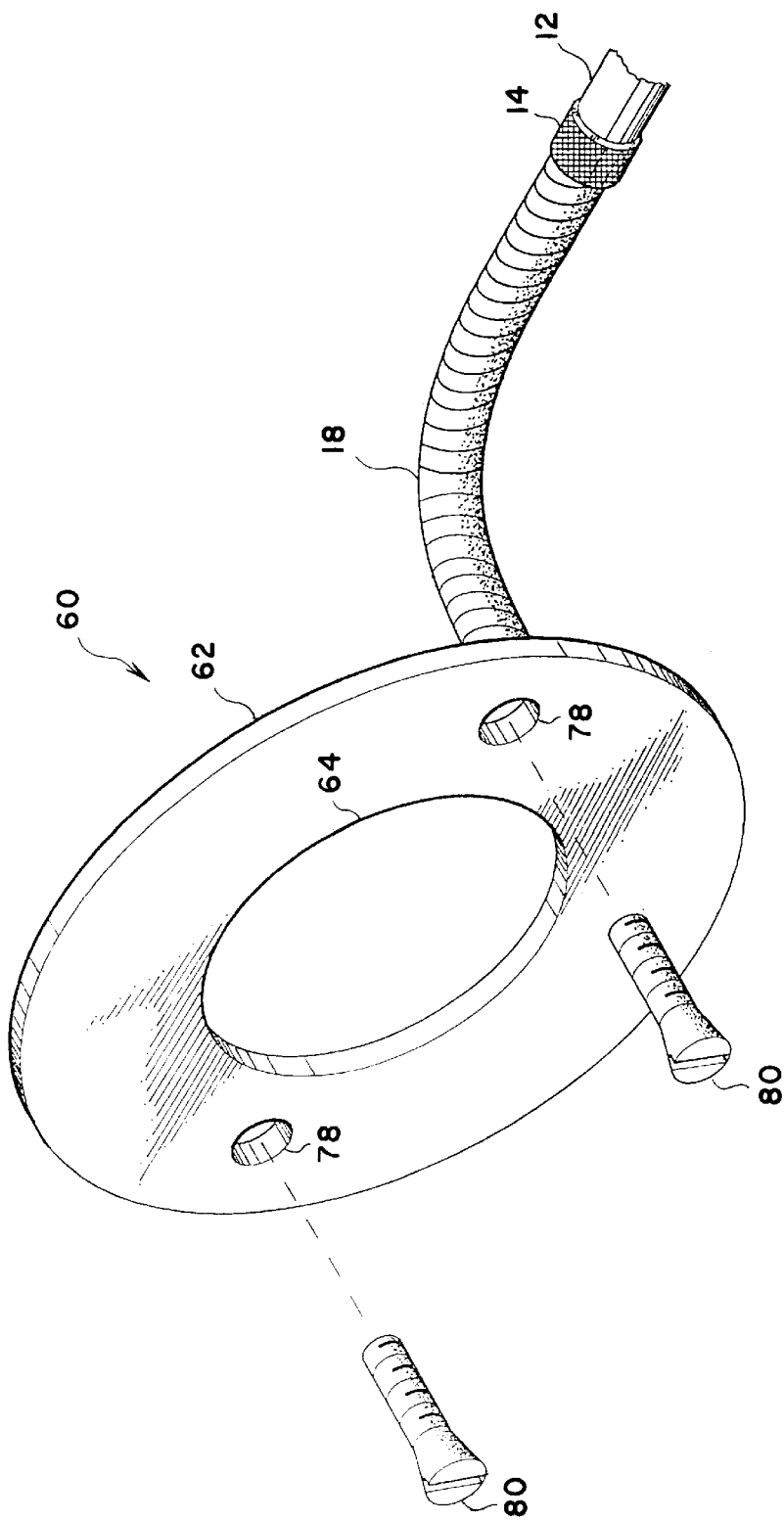
FIG. 12 is a perspective view of the circular sample collection attachment attached to the flexible swabbing tool.

FIG. 11 is a perspective view of the circular sample collection attachment 60, as seen from its rear, having a circular template 62 with hole 64 of a known area. A swab on another handle must be used to take a sample within the hole of a surface which the template is held against. As the hole has a fixed area, the contamination for the entire surface can be extrapolated from that in the hole. The circular sample collection attachment also has a cylindrical member 66 with a fixed peg 68 and a depressible peg 70, so that it can be retained within the aforementioned socket. The cylindrical member 66 is attached to the center of an U-shaped member 72 which is attached at its two ends to poles 76 attached to disks 74 attached to the circular template. FIG. 12 is a perspective view of the circular sample collection attachment, as seen from its front, attached to the flexible swabbing tool, showing two bolt holes 78 and bolts 80 by which the circular template is attached to the poles of the opposite side.

Figure 13:
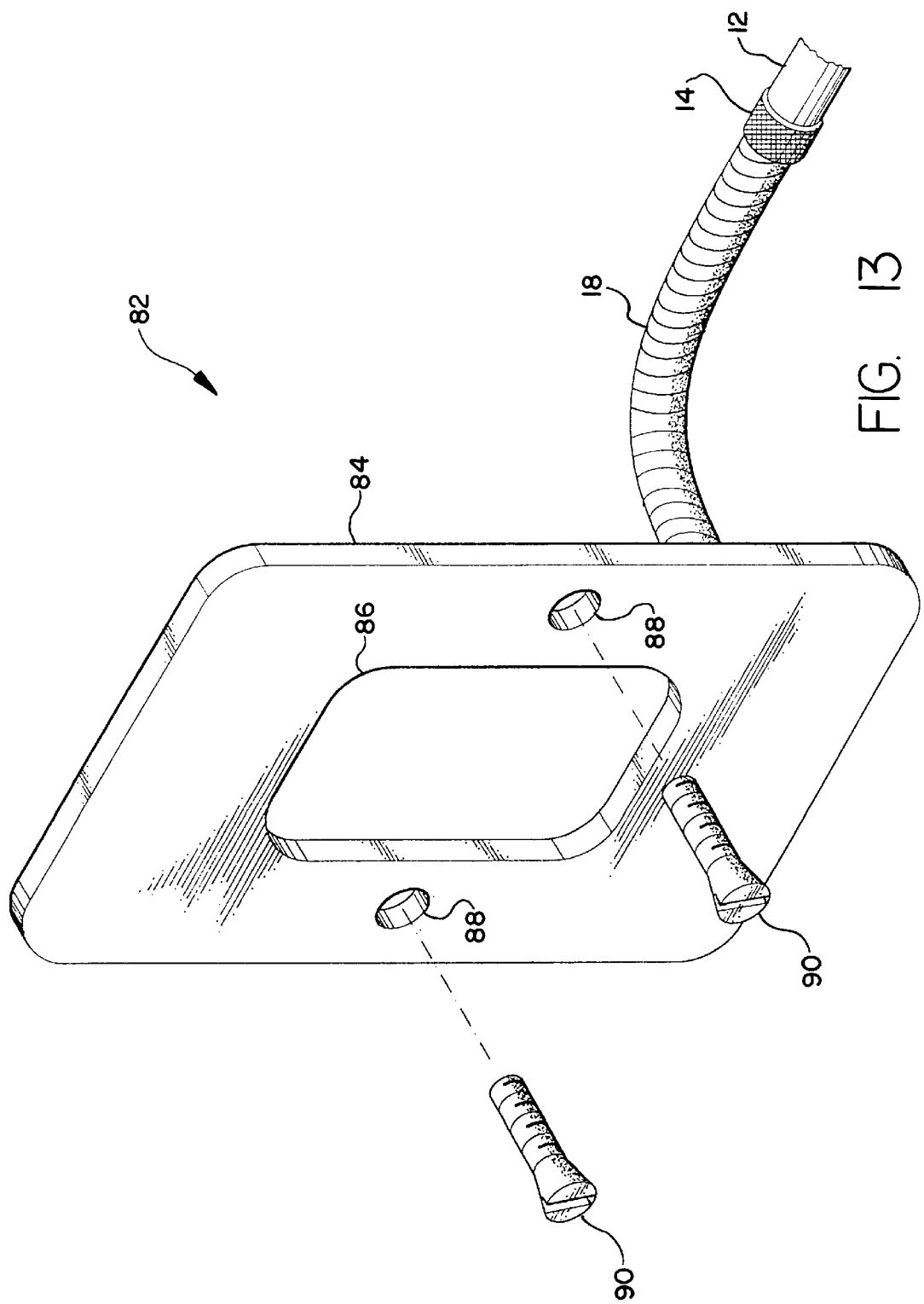
FIG. 13 is a perspective view of the rectangular sample collection attachment attached to the flexible swabbing tool.

FIG. 13 is a perspective view of the rectangular sample collection attachment 82 attached to the flexible swabbing tool. It has a rectangular template 84 with a rectangular hole 86 with a defined area, within which a sample of the surface that the template is held against is taken, as with the circular sample collection attachment. It also has two bolt holes 88 with two bolts 90 by which the template is attached.

FIG. 14 is a top view of the circular sample collection attachment 60 attached to the flexible swabbing tool, showing more clearly how the circular template 62 is attached to the disks 74 attached to the poles 76 attached to the U-shaped member attached to the cylindrical member 66 with the fixed peg 68 that fits within the curved notch 48 of the socket 20 attached to the flexible tubular extension 18.

Other kinds of swabs than those shown in the drawings may also be used with the clamp attachment, including cylindrical sponges, that may be retained in sealed plastic bags or glass bottles until they are used, to prevent contamination.

It is to be understood that the present invention is not limited to the embodiments described above, but encompasses any and all embodiments within the scope of the following claims.

I claim:

1. A swabbing tool comprising:
    a flexible tubular member having a first end and a second end;
    a telescoping tubular handle attached to the second end of said flexible tubular member;
    a cylindrical socket attached to the first end of said flexible tubular member, said socket having a J-shaped notch;
    a clamp attachment including an upper member pivotally connected to a lower member, said upper member and said lower member each including a front end defining a jaw having a contact surface with a length and a relatively narrow width, said clamp attachment further including spring means for biasing the front end of the upper member toward the front end of the lower member, said upper member and said lower member each including a recess extending adjacent the length of each jaw and a central notch along the width of each jaw and extending perpendicular to the recess along said lower member; and
    a cylindrical member extending from said lower member and insertable in said socket, said cylindrical member having a closed planar end and a circumferential surface, said planar end including a depressible peg and said circumferential surface includes a fixed ped; whereby,
    upon insertion of the cylindrical member into the socket, the fixed peg engages the J-shaped notch and the depressible ped is pushed inward to securely retain the clamp attachment.

2. A swabbing tool according to claim 1, further including a swab attachment securably connectable to said clamp attachment, said swab attachment having a cylindrical handle for retention within the central notch of the clamp attachment.

3. A swabbing tool according to claim 2, wherein said swab attachment includes a polyester swab.

4. A swabbing tool according to claim 2, wherein said swab attachment includes a suction cup holding a sample collecting plate.

5. A swabbing tool according to claim 4, wherein said sample plate includes a layer of culture medium for collecting microorganisms.

* * * * *